United States Patent [19]

Cox et al.

[11] Patent Number: 5,123,281

[45] Date of Patent: Jun. 23, 1992

[54] ULTRASONIC TESTING DEVICE

[75] Inventors: Loran D. Cox; Thomas R. Larson, both of Bedford, Tex.

[73] Assignee: General Dynamics Corporation, Fort Worth, Tex.

[21] Appl. No.: 512,669

[22] Filed: Apr. 20, 1990

[51] Int. Cl.$^5$ .............................................. G01N 29/28
[52] U.S. Cl. ............................................. 73/644; 73/633
[58] Field of Search .................. 73/644, 632, 633, 637, 73/638, 622

[56] References Cited

U.S. PATENT DOCUMENTS

| | | | |
|---|---|---|---|
| 3,255,626 | 6/1966 | Van Der Veer | 73/644 |
| 3,672,211 | 6/1972 | Hatch | 73/633 |
| 4,033,178 | 7/1977 | Holt et al. | 73/644 |
| 4,510,812 | 4/1985 | Feng | 73/644 |
| 4,587,849 | 5/1986 | Gross | 73/644 |

FOREIGN PATENT DOCUMENTS

| | | | |
|---|---|---|---|
| 1287817 | 1/1969 | Fed. Rep. of Germany | 73/644 |
| 2312032 | 12/1976 | France | 73/644 |
| 426187 | 10/1974 | U.S.S.R. | 73/644 |

*Primary Examiner*—John E. Chapman
*Attorney, Agent, or Firm*—James E. Bradley

[57] ABSTRACT

An apparatus for ultrasonically testing a part uses a transducer which emits sound waves to flow through a water column into contact with the part. The housing has sidewalls, a top, and a bottom, defining a reservoir. The transducer locates in the reservoir and points downward toward the bottom. A collar extends upward from the bottom in alignment with the transducer. The collar has an open upper end spaced a selected distance above the bottom. A tube mounts in the collar in alignment with the transducer. The tube will slide vertically relative to the collar. The lower end of the tube protrudes through an aperture in the bottom for contact with the part. Water is supplied to the reservoir, to flow over the upper end of the collar and through the tube against the part. A supporting surface on the housing supports the housing on the part and depends downward from the bottom of the housing.

18 Claims, 1 Drawing Sheet

ULTRASONIC TESTING DEVICE

This invention was made with Government support under Contract No. N00019-88-C-0050 awarded by Department of the Air Force. The Government has certain rights in this invention.

BACKGROUND OF THE INVENTION

1. Field of the Invention

This invention relates in general to ultrasonic testing devices, and in particular to a device that holds an ultrasonic transducer and receives and discharges water against a part being ultrasonically tested.

2. Description of the Prior Art

Laminated components, particularly those for aircraft parts, must be tested for proper bonding of the various layers. Manufacturers utilize ultrasonic test equipment for testing the bonding. In ultrasonic testing, a transducer will transmit a sound wave through liquid against the surface of the part. The transducer receives reflections back. The testing unit will analyze the reflections to determine whether proper bonding has occurred.

The ultrasonic transducer and the part to be tested can be submerged for this testing. This is not always practical nor convenient.

In another technique, the transducer will be coupled to the part being tested by an oil or a water based gel. A disadvantage of this technique is that there is a tendency for the oil or gel to disburse over the part. It becomes difficult to maintain the ultrasonic signal. Further, when moving the transducer over the part, it is easily rocked or tipped, therefore losing normality to the part and thus losing the ultrasonic signal. Also, the plastic tips of the devices will wear and become rough and rounded, which creates further difficulties with the signal.

In another technique, the transducer will be mounted in a nozzle. The nozzle discharges a water column under pressure against the part. A disadvantage of this system is the resulting noise that occurs due to the water flow. Air bubbles and turbulence will create noise. Also, the contours of complex shaped parts to be tested must be followed. This makes maintaining normality to the part difficult.

SUMMARY OF THE INVENTION

The device of this invention is a hand held unit. It has a housing with a supporting surface for placing directly against the part. In one embodiment, the supporting surface spaces the bottom of the housing a slight distance from the part. The housing has a large reservoir in which a liquid, normally water, will be supplied.

A tube mounts in the reservoir, with its lower end protruding through the bottom into contact with the part. The tube will slide vertically in the housing to accommodate roughness of the part being tested.

The water flow will be at a low rate because of low input pressure to the reservoir. A collar extends upward from the bottom of the housing a selected distance. The tube will be carried in this collar. The water must flow over the upper end of the collar and down the tube.

DETAILED DESCRIPTION OF THE INVENTION

Figure 1:
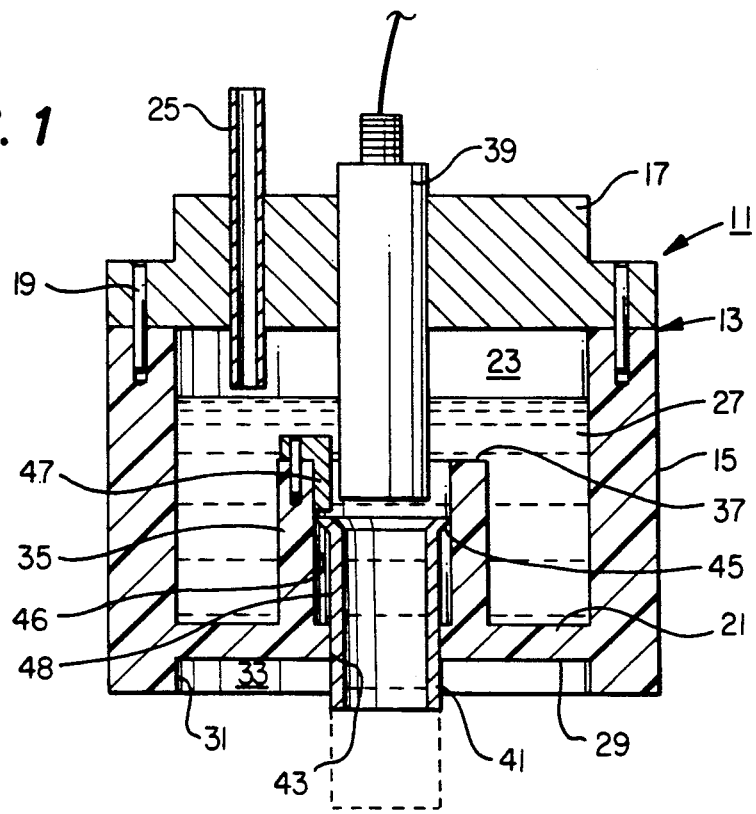
FIG. 1 is a vertical cross-sectional view of an ultrasonic testing device constructed in accordance with this invention.

Referring to FIG. 1, the testing device 11 includes a housing 13. Housing 13 has upright or vertical sidewalls 15. In the embodiment of FIG. 1, the sidewalls 15 comprise a cylinder. A top 17 mounts to the upper end by means of fasteners 19. The housing 13 and top 17 are preferably constructed of Teflon.

Housing 13 has a horizontal bottom 21. The bottom 21, sidewalls 15 and top 17 define a chamber or reservoir 23. An inlet tube 25 extends through the top 17 for supplying liquid 27, which normally will be water. The pressure of the water flowing through inlet tube 25 will be low, preferably in the range from 2-5 psi (pounds per square inch).

Bottom 21 has a lower surface 29 that faces downward. A supporting surface 31 extends completely around the periphery of the bottom 21. This supporting surface 31 is a lip or wall depending downward from the lower surface 29. The supporting surface 31 is adapted to contact or support the housing 13 on a part (not shown) to be tested. The lower edge of supporting surface 31 will be located in a single plane in the embodiment of FIGS. 1 and 2. Supporting surface 31 defines a cavity 33 below the lower surface 29 and above the part to be tested. The lower surface of supporting surface 31 is smooth with a low coefficient of friction.

A collar 35 extends upward from the bottom 21. Collar 35 is a tubular member integrally formed with the bottom 21. Collar 35 has an upper end 37 that is located a substantial distance below the top 17, and slightly more than midway up the vertical height of the sidewalls 15.

An ultrasonic transducer 39 mounts rigidly to the top 17. Transducer 39 is conventional. It is a cylindrical member with a lower end that faces downward. It will be in vertical alignment with the collar 35. The lower end of the transducer 39 will extend a short distance into the collar 35. Transducer 39 will be connected to an analyzing unit (not shown) of conventional nature.

A rigid, lightweight, metal tube 41 mounts concentrically within the collar 35. The mounting means for the tube 41 includes an aperture 43 formed in the housing bottom 21. Aperture 43 is slightly larger in diameter than the tube 41 so as to allow the tube 41 to freely slide vertically or along the axis of the tube 41. The dotted lines indicate a lower position of the tube 41, with the tube 41 being shown in position close to its uppermost position.

Tube 41 has open upper and lower ends and a rim 45 on its upper edge. Rim 45 extends radially outward from the tube and will slidingly engage the inner wall 46 of the collar 35. The outer diameter of the remaining portion 48 of the tube 41 below the rim 45 will not touch the inner wall 46. The rim 45 serves as part of the mounting means to guide the tube 41 for vertical sliding movement relative to housing 13.

A stop 47 secures to the upper end 37 of collar 35. Stop 47 limits the upward travel of the tube 41. The protruding rim 45 retains the tube 41 within the collar 35 because the rim 45 has an outer diameter greater than the diameter of the aperture 43.

In operation, the device 11 will nearly always be operated in a vertical or near vertical position. The housing 13 will rest on the part. The supporting surface 31 will support the housing 13 on the part with the bottom lower side 29 spaced above the part. The tube 41 will drop by gravity until its lower end touches the surface of the part to be tested. Water 27 at a low pressure will be delivered through the inlet 25 into the reservoir 23.

Water 27 will fill reservoir 23 to a level above the upper end 37 of the collar 35 and will flow down through the tube 41 into contact with the part. It is not necessary that the reservoir 23 be completely filled for the device 11 to operate. As the water 27 flows down the tube 41, some of the water will leak out past the lower end of the tube 41 The lower end of tube 41 does not form a tight seal with the part being tested; rather the tube 41 remains in contact with the part due to force of gravity and possibly some force due to water moving downward through the tube 41.

The water leaked from the lower end of tube 41 will flow into the cavity 33. Also, some of the water from the cavity 33 will leak past the supporting surface 31 because the supporting surface 31 will not form a tight seal with the part being tested.

The operator will energize the ultrasonic transducer 39 to transmit sound waves through the water 27 contained within the tube 41. The sound waves strike the part being tested and reflect back from the part. The transducer 39 will detect these sound waves. A testing unit (not shown) will make a record and analysis.

The operator will move the testing device 11 over the surface of the part. If the part has a rough surface, the tube 41 will move up and down slightly relative to the housing 13 to accommodate the irregularities in the surface of the part.

Figure 2:
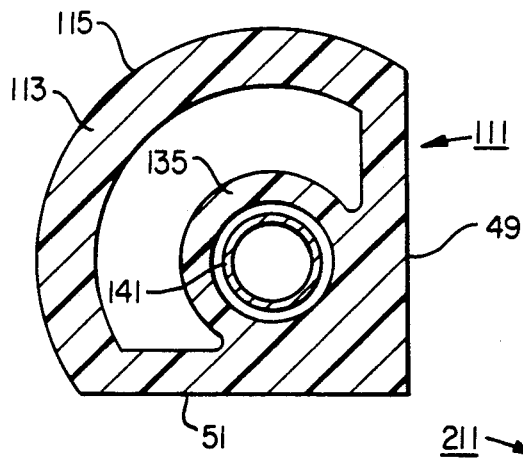
FIG. 2 is a transverse cross-sectional view of an alternate embodiment of an ultrasonic testing device constructed in accordance with this invention.

In the embodiment of FIG. 2, the device 111 will operate in the same manner as the device 11. However it differs in that the sidewalls 115 of housing 13 are not completely cylindrical, rather, the cylindrical portion extends only about 90 degrees. It will have two flat vertical sidewalls 49, 51. The sidewalls 49, 51 intersect each other, forming a 90 degree corner. The collar 135 will not be concentric in the housing 113 and will not comprise a complete cylindrical surface. The tube 141 will be the same as the tube 41. The flat sidewalls 49, 51 enable the unit to be placed close to upright surfaces on the part being tested.

Figure 3:
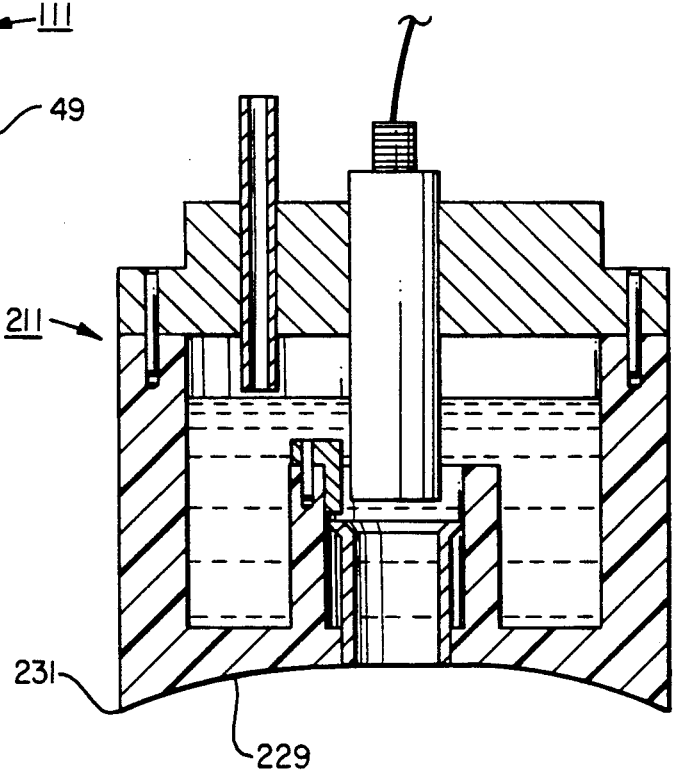
FIG. 3 is a vertical cross-sectional view of a second alternate embodiment of an ultrasonic testing device constructed in accordance with this invention.

In the embodiment of FIG. 3, the device 211 is the same as in the embodiment of FIG. 1, except the lower surface 229 is arcuate and a segment of a cylinder, rather than flat as the lower surface 29. There will be two straight, parallel side edges 231, rather than the cylindrical wall of the supporting surface 31 in the embodiment of FIG. 1. Device 211 will be used to test cylindrical parts, such as pipes. The radius of the surface 229 should be the same as the radius of the pipe being tested. The surface 229 will rest directly on the pipe. There will not be any cavity 33.

The invention has significant advantages. The low velocity water column maintains a more consistent couple than oils or gels. Because of the extremely low velocity, there is no water turbulence to create noise. The low friction smooth material of the supporting surface of the housing reduces wear that occurs with prior art tips. The device allows one to maintain an immersion quality standard on rough surfaces. The device is readily portable.

While the invention has been shown in only three of its forms, it should be apparent to those skilled in the art that it is not so limited, but is susceptible to various changes without departing from the scope of the invention.

We claim:

1. In an apparatus for ultrasonically testing parts, the apparatus being of the type having a housing with an inlet and an outlet for liquid discharge, and an ultrasonic transducer mounted in the housing and facing the outlet for transmitting sound waves through the liquid to the part and receiving reflections, the improvement comprising:
    supporting surface means on the housing for supporting the housing on the part;
    a tube having open upper and lower ends; and
    mounting means for mounting the tube in the outlet of the housing for vertical sliding movement relative to the housing and supporting surface means, with the upper end of the tube spaced below the transducer and the lower end adapted to contact the part for liquid discharge through the tube against the part, the vertical sliding movement allowing the tube to follow the contour of the part.

2. The apparatus according to claim 1 wherein the housing has a bottom through which the tube extends, the bottom being spaced above the supporting surface means, causing the tube to protrude from the bottom when in contact with the part.

3. The apparatus according to claim 1 wherein the housing has a bottom and wherein the supporting surface means depends downward from the bottom and extends continuously around the bottom, defining a cavity, the tube protruding from the bottom through the cavity.

4. An apparatus for ultrasonically testing a part, comprising in combination:
    a housing having sidewalls, a top, and a bottom, defining a reservoir;
    supporting surface means comprising a depending supporting wall extending downward from the bottom of the housing and having a lower edge for supporting the housing on the part, with the bottom located above the part, the supporting wall extending continuously around the bottom, defining a cavity;
    an ultrasonic transducer located in the reservoir, the transducer being mounted to the top and pointing downward toward the bottom;
    a collar located in the reservoir and extending upward from the bottom in alignment with the transducer, the collar having an opening spaced a selected distance above the bottom;
    a tube having open upper and lower ends;
    mounting means for mounting the tube in the collar in alignment with the transducer, with the upper end of the tube below the opening of the collar and the lower end of the tube protruding through bottom for contact with the part as the supporting wall supports the housing on the part; and
    inlet means in the housing for supplying liquid to the reservoir to flow through the opening of the collar and through the tube against the part, with some of the liquid filling the cavity defined by the supporting wall.

5. An apparatus for ultrasonically testing a part, comprising in combination:
- a housing having sidewalls, a top, and a bottom, defining a reservoir;
- supporting surface means extending downward from the bottom of the housing and having a lower edge for supporting the housing on the part, with the bottom located above the supporting surface means;
- an ultrasonic transducer located in the reservoir, the transducer being mounted to the top and pointing downward toward the bottom;
- a collar located in the reservoir and extending upward from the bottom in alignment with the transducer, the collar having an opening spaced a selected distance above the bottom;
- a tube having open upper and lower ends;
- mounting means for mounting the tube in the collar in alignment with the transducer, with the upper end of the tube below the opening of the collar and the lower end of the tube protruding through bottom for contact with the part as the supporting surface means supports the housing on the part;
- inlet means in the housing for supplying liquid to the reservoir to flow through the opening of the collar and through the tube against the part; and
- wherein the mounting means mounts the tube for free vertical sliding movement of the tube relative to the collar, to allow the tube to freely move up and down relative to the housing to follow irregularities in the surface of the part.

6. The apparatus according to claim 4, wherein the mounting means allows the lower end of the tube to locate above the lower edge of the supporting wall if the contour of the part protrudes into the space between the lower edge of the supporting wall and the bottom.

7. An apparatus for ultrasonically testing a part, comprising in combination:
- a housing having sidewalls, a top, and a bottom, defining a reservoir;
- supporting surface means extending downward from the bottom of the housing and having a lower edge for supporting the housing on the part, with the bottom located above the supporting surface means;
- an ultrasonic transducer located in the reservoir, the transducer being mounted to the top and pointing downward toward the bottom;
- a collar located in the reservoir and extending upward from the bottom in alignment with the transducer, the collar having an opening spaced a selected distance above the bottom;
- a tube having open upper and lower ends;
- mounting means for mounting the tube in the collar in alignment with the transducer, with the upper end of the tube below the opening of the collar and the lower end of the tube protruding through bottom for contact with the part as the supporting surface means supports the housing on the part;
- inlet means in the housing for supplying liquid to the reservoir to flow through the opening of the collar and through the tube against the part; and
- wherein the mounting means mounts the tube for free vertical sliding movement of the tube relative to the collar and allows the lower end of the tube to move above the lower edge of the supporting surface means if the contour of the part protrudes into the space between the lower edge of the supporting surface means and the bottom.

8. The apparatus according to claim 4 wherein at least one of the sidewalls is flat and vertical to enable the apparatus to be moved close to any upright surfaces on the part.

9. The apparatus according to claim 4 wherein two of the sidewalls are flat and vertical and intersect each other in a 90 degree corner to enable the apparatus to be moved close to upright corner surfaces on the part.

10. An apparatus for ultrasonically testing a part which has a cylindrical configuration, comprising in combination:
- a housing having a bottom adapted to be placed on the part, the housing also having sidewalls and a top, defining a reservoir;
- an ultrasonic transducer located in the reservoir, the transducer being mounted to the top and pointing downward toward the bottom;
- a collar located in the reservoir and extending upward from the bottom in alignment with the transducer, the collar having an opening spaced a selected distance above the bottom;
- a tube having open upper and lower ends;
- mounting means for mounting the tube in the collar in alignment with the transducer, with the upper end of the tube below the opening of the collar and the lower end of the tube protruding through bottom for contact with the part as the bottom supports the housing on the part;
- inlet means in the housing for supplying liquid to the reservoir to flow through the opening of the collar and through the tube against the part; and
- wherein the bottom of the housing is an arcuate recess in the configuration of a cylinder for mating with the cylindrical configuration of the part.

11. An apparatus for ultrasonically testing a part, comprising in combination:
- a housing having sidewalls, a top, and a bottom, defining a reservoir, the bottom having an aperture;
- an ultrasonic transducer located in the reservoir, the transducer being mounted to the top and pointing downward toward the bottom;
- a collar located in the reservoir and extending upward from the bottom in alignment with the transducer, the collar having an open upper end spaced a selected distance above the bottom;
- a tube having open upper and lower ends;
- mounting means for mounting the tube in the collar in alignment with the transducer and for vertical sliding movement relative to the collar, with the upper end of the tube below the upper end of the collar and the lower end of the tube protruding through the aperture in the bottom for contact with the part;
- inlet means in the housing for supplying liquid to the reservoir, to flow over the upper end of the collar and through the tube against the part; and
- a supporting surface on the housing for supporting the housing on the part, the supporting surface depending downward from the bottom and extending continuously around the bottom, defining a cavity which fills with some of the liquid discharged from the tube.

12. The apparatus according to claim 11 wherein the bottom has a lower side which is flat, and wherein the supporting surface comprises a lip formed on the edges of the bottom.

13. The apparatus according to claim 11 wherein the tube is rigid.

14. The apparatus according to claim 11 wherein the tube is cylindrical and has a constant diameter but for a radially protruding rim on its upper end which is of greater diameter than the aperture.

15. A method of ultrasonically testing parts, comprising in combination:
providing a supporting surface;
mounting a tube to the supporting surface for vertical sliding movement relative to the supporting surface;
mounting an ultrasonic transducer above the tube;
placing the supporting surface on the part and placing the lower end of the tube in contact with the part;
supplying liquid to the tube to flow out the tube onto the part;
emitting sound waves from the transducer to pass through the tube into contact with the part and detecting reflections; and
moving the supporting surface and the tube across the part and allowing the tube to move vertically slightly relative to the supporting surface to accommodate roughness in the part.

16. The method according to claim 15 wherein the liquid is supplied to the tube at a pressure within the range from 2 to 5 psi.

17. A method of ultrasonically testing parts, comprising in combination:
providing a housing with a reservoir, with a bottom and with a supporting surface on the bottom;
mounting an ultrasonic transducer in the housing;
mounting a tube in the bottom of housing for vertical sliding movement relative to the housing;
placing the supporting surface on the part;
allowing the lower end of the tube to drop by gravity into contact with the part;
supplying liquid to the reservoir and causing the liquid to flow out the tube onto the part;
emitting sound waves from the transducer to pass through the tube into contact with the part and detecting reflections; and
moving the supporting surface and the tube across the part and allowing the tube to move vertically slightly relative to the housing and supporting surface to accommodate roughness in the part.

18. The method according to claim 17 wherein the liquid is supplied to the reservoir at a pressure within the range from 2 to 5 psi.

* * * * *